United States Patent [19]

Petr et al.

[11] Patent Number: 4,752,733
[45] Date of Patent: Jun. 21, 1988

[54] COMPENSATING CIRCUIT FOR A MAGNETIC FIELD SENSOR

[76] Inventors: Jan Petr, Stolzengrabenstr. 33, CH-6317 Oberwil; Heinz Lienhard, Rosenbergweg 14, CH-6300 Zug, both of Switzerland

[21] Appl. No.: 765,057

[22] Filed: Aug. 12, 1985

[30] Foreign Application Priority Data

Aug. 16, 1984 [CH] Switzerland ............ 935/84

[51] Int. Cl.$^4$ .............. G01N 27/72; G01R 33/06; H01L 43/06
[52] U.S. Cl. ............... 324/225; 324/251; 307/309; 338/32 H
[58] Field of Search ........ 324/225, 251, 252; 307/309; 338/32 H, 32 R

[56] References Cited

U.S. PATENT DOCUMENTS 3,219,909 11/1965 Foster .................. 324/251

FOREIGN PATENT DOCUMENTS

0137896 4/1985 European Pat. Off. .
2621302 9/1980 Fed. Rep. of Germany .
1124576 8/1968 United Kingdom .

Primary Examiner—Reinhard J. Eisenzopf
Assistant Examiner—Walter E. Snow

[57] ABSTRACT

A circuit which compensates for fluctuations in the transfer characteristic of a magnetic field sensor is disclosed. More particularly, an auxiliary magnetic field is generated preferably by a coil which is connected to a voltage generator by way of a voltage/current transducer. The auxiliary magnetic field along with the magnetic field to be measured is detected by the magnetic field sensor. The portion of the sensor output signal due to the auxiliary magnetic field is correlated with the voltage produced by the voltage generator by means of a correlator circuit. If the portion of the magnetic field sensor output due to the auxiliary magnetic field is not properly correlated with the signal from the voltage generator a feedback signal is sent to the magnetic field sensor to adjust the transfer characteristic.

11 Claims, 3 Drawing Sheets

COMPENSATING CIRCUIT FOR A MAGNETIC FIELD SENSOR

FIELD OF THE INVENTION

This invention relates to a circuit for the compensation of fluctuations in the transfer characteristic of a magnetic field sensor.

BACKGROUND OF THE INVENTION

It has been known to measure an electric current in a potential-free manner by the magnetic field that the current produces. To determine the strength of the magnetic field, a semiconductor element that produces a voltage output more or less proportional to the magnetic field to be measured may be used. Such semiconductor devices include Hall effect devices and magnetotransistors. One problem with such devices is that there may be fluctuations in the transfer factor (i.e. transfer characteristic) between the magnetic field to be measured and the output voltage. In order to suppress the influence of such fluctuations in the transfer factor of the magnetic field sensor, a magnetic counter-field may be originated by means of a magnetic coil with magnetic counter-field virtually wholly compensates (i.e. cancels) the magnetic field to be measured (DE-AS No. 26 21 302). One disadvantage of such compensated transducers is the relatively high performance requirement needed to originate the compensating magnetic field.

In Swiss patent application No. 4,448/83-2, a circuit is described in which an auxiliary magnetic field of known magnitude is superimposed on a magnetic field to be measured by means of a magnetic coil. The transfer characteristic curve of the magnetic field sensor is determined solely by the portion of the auxiliary magnetic field in the output signal. The output signal of the magnetic field sensor is divided by the thus determined slope to calculate the magnetic field.

This invention has the object to create a circuit of the afore-described type that is economical to operate and does not have a high performance requirement for originating a compensating auxiliary magnetic field, and wherein no determination of a slope of the transfer characteristic of a magnetic field sensor is required. It is a further object of the present invention to provide a circuit which compensates for fluctuations in the transfer characteristic (i.e. the transfer factor) of a magnetic field sensor.

SUMMARY OF THE INVENTION

The present invention is a circuit which compensates for fluctuations in the transfer characteristic of a magnetic field sensor. More particularly, an auxiliary magnetic field is generated, preferably by a coil which is connected to a voltage generator by way of a voltage/current transducer. The auxiliary magnetic field along with the magnetic field to be measured is detected by the magnetic field sensor. In a preferred embodiment of the invention, a signal resulting at least in part from the detection of the auxiliary magnetic field by the magnetic field sensor is correlated with the signal produced by the voltage generator by means of a correlator circuit. If the portion of the magnetic field sensor output due to the auxiliary magnetic field is not appropriately correlated with the signal from the voltage generator a feedback signal is sent to the magnetic field sensor to adjust the transfer characteristic.

BRIEF DESCRIPTION OF THE DRAWINGS

In all Figures the same numerals serve to designate like parts.

DETAILED DESCRIPTION OF THE INVENTION

Figure 1:
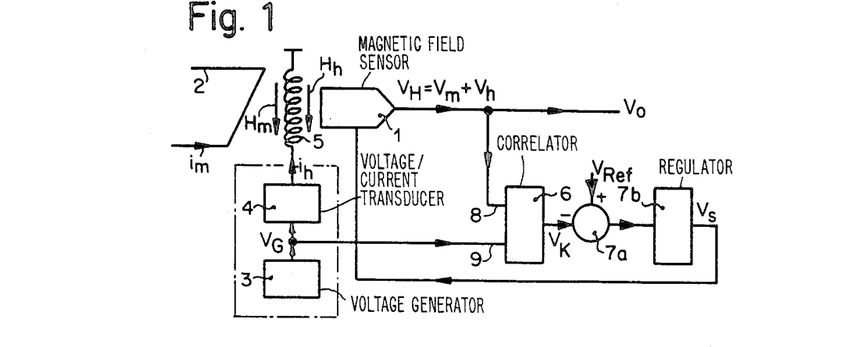
FIG. 1 shows a block diagram of a first variant of a circuit for the compensation of fluctuations in the transfer characteristic of a magnetic field sensor, in accordance with an illustrative embodiment of the invention.

In FIG. 1, the numeral 1 designates a conventional magnetic field sensor such as a Hall element or a magnetotransistor. The magnetic field sensor 1 serves to measure a current $i_m$ that flows in an electric conductor 2 by means of the magnetic field $H_m$ resulting from the current $i_m$. The coupling of the magnetic field $H_m$ originated by the current to be measured $i_m$ into the magnetic field sensor 1 can be accomplished in a known manner by means of a magnetic core, or alternatively without a magnetic core by arranging the magnetic field sensor 1 on the surface of conductor 2 which may be formed as a flat conductor. The magnetic field sensor 1 delivers at its output a voltage $V_H$ that depends on the magnetic field $H_m$, working thus as a magnetic field-/voltage-transducer. The transfer characteristic curve of the magnetic field sensor 1 is a function of temperature, being, in addition, subjected to fluctuations due to aging so that an exact measurement of the magnetic field $H_m$ is not possible without taking special steps.

Besides the magnetic field sensor 1, the switching circuit illustrated in FIG. 1 comprises a voltage generator 3, a voltage/current-transducer 4, a coil 5, a correlator circuit 6, a first difference circuit 7a and a regulator 7b. The regulator 7b may, for example, be an integrating regulator. The output of the voltage generator 3 is connected to the input of the voltage/current-transducer 4. The voltage generator 3 and the voltage/current-transducer 4 together form a voltage/current generator 3;4, whose current output is connected to one terminal of the coil 5 for the origination of an auxiliary magnetic field $H_h$ which is superimposed on the magnetic field $H_m$. The other terminal of the coil 5 is connected to ground. The voltage/current generator 3;4 has, in addition, an output for the voltage $V_G$, which is simultaneously the output of the voltage generator 3. The conductor 2 and the coil 5 are spatially arranged in such a way that the magnetic fields $H_m$ and $H_h$ have, at least approximately, the same direction.

Correlator 6 has two inputs, of which the first input 8 is the output voltage $V_o$ of the magnetic field sensor 1 while the second input 9 is connected to the voltage output $V_G$ of voltage/current generator 3;4. The output of correlator 6 is connected, for example, to the minus input of a first difference circuit 7a, whose output, in turn, is connected to the input of regulator 7b. The plus-input of the first difference circuit 7a is a reference voltage $V_{Ref}$. The output of regulator 7b is connected to a control input of the magnetic field sensor 1 which influences the transfer characteristic of magnetic field sensor 1. The output $V_o$ of magnetic field sensor 1 constitutes simultaneously the output of the circuit illustrated in FIG. 1.

The described circuit operates as follows. The output voltage $V_G$ of voltage generator 3 generates the auxiliary magnetic field $H_m$ with the aid of the proportional auxiliary current $i_h$ and the coil 5 traversed by the auxiliary current $i_h$. The auxiliary magnetic field $H_h$ has a known time dependency as well as a known magnitude. The amplitude of the auxiliary magnetic field $H_h$ is, in practice, only a few percent of the maximum value of the amplitude of the magnetic field $H_m$ to be measured, so that no demanding performance requirement is necessary to originate the auxiliary magnetic field $H_h$.

The magnetic field sensor 1 converts the two magnetic fields $H_m$ and $H_h$ into the output voltages $V_m$ and $V_h$, respectively, so that that the output voltage $V_H$ of the magnetic field sensor 1 equals the sum $(V_m+V_h)$, which feeds the first input 8 of the correlator circuit 6. Correlator 6 correlates the voltage $V_H = V_m + V_h$ with the output voltage $V_G$ of the voltage generator 3, which originally produces the auxiliary magnetic field $H_h$ and, thereby, also the voltage $V_h$. If the fields $H_h$ and $H_m$ have no frequency components in common (for example if the frequency of $H_m$ is an even multiple of frequency of $H_h$), the output of the correlator 6 is dependent on the correlation between $V_h$ and $V_G$. If there are non-linear fluctuations or other variations in the transfer characteristic of the magnetic field sensor 1 $V_h$ and $V_G$ will be somewhat decorrelated. This will be reflected in the output voltage $V_K$ of the correlator 6. The voltage $V_K$ is compared to a reference voltage $V_{Ref}$ by comparator 7a. Illustratively $V_K$ equals $V_{Ref}$ when $V_h$ and $V_G$ are properly correlated and there are no fluctuations in the transfer characteristic of the magnetic field sensor. If $V_K$ and $V_{Ref}$ are not equal, regulator 7b transmits a signal to a control input of the magnetic field sensor 1, to adjust the transfer characteristic thereof.

The control loop 1; 6; 7a; 7b serves to maintain constant the voltage $V_K$ and thereby also a constant transfer characteristic of the magnetic field sensor 1. Since the magnetic field sensor 1 has an essentially equal transfer factor for the two magnetic fields $H_m$ and $H_h$, this means that the transfer factor for the magnetic field $H_m$ to be measured is compensated for fluctuations due to temperature and age.

Figure 2:
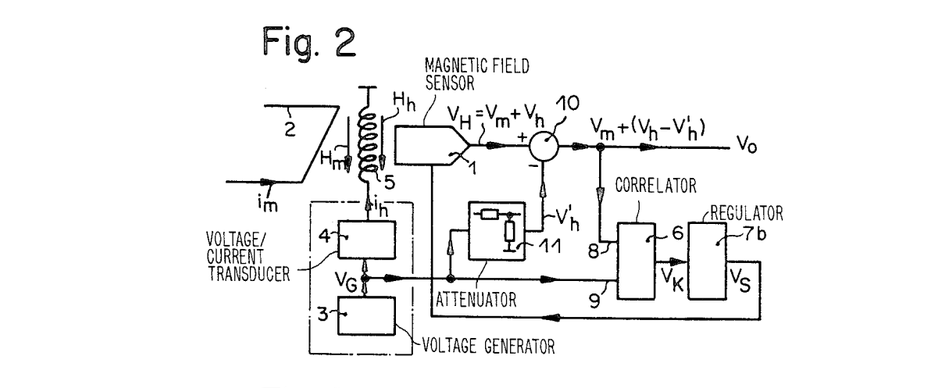
FIG. 2 shows a block diagram of a second variant of such a circuit in accordance with an illustrative embodiment of the invention.

The circuit illustrated in FIG. 2 corresponds approximately to the circuit of FIG. 1, with the exception that the output of magnetic field sensor 1 is not connected directly with the first input 8 of correlator 6. Instead, the output $V_H = V_m + V_h$ of magnetic field sensor 1 is illustratively connected to the plus-input of a second difference circuit 10. The minus input of the second difference circuit 10 is connected to the voltage output of the voltage/current generator 3;4 by way of attenuator 11. The output of the second difference circuit is connected to the input 8 of the correlator circuit 6. The output of the second difference circuit 10 is simultaneously the output $V_o$ of the arrangement illustrated in FIG. 2.

The arrangement of FIG. 2 operates similarly to the arrangement illustrated in FIG. 1, with the exception that here, with the aid of the second difference circuit 10, the output voltage $V'_h = k \cdot V_G$ of the resistive member 11 is subtracted from the output voltage $V_H = V_m + V_h$ of the magnetic sensor 1 before it is conducted to the correlator 6 and the output of the switching circuit. k represents the transfer factor of attenuator 11. Thus, there results the question:

$$V_o = (V_m + V_h) - V'_h = V_m + \Delta V_h \text{ with}$$

$$\Delta V_h = V_h - V'_h = V_h - k V_G.$$

There are two different paths of transfer for the output voltage $V_G$ of the voltage generator 3: on the one hand, it reaches the output of difference circuit 10 as voltage $V_h$ over the voltage/current transducer 4, the coil 5 and the magnetic field sensor 1 and, on the other hand, as voltage $V'_h$ over the attenuator 11. The transfer factor k for the attenuator 11 may be chosen so that the transfer factors for these two paths are equal, in which case $\Delta V_h = 0$ and $V_o = V_m$. The output voltage of the switching circuit represented in FIG. 2, thus, no longer comprises the voltage $V_h$ originated by the auxiliary magnetic field $H_h$. Fluctuations attributable to temperature of aging in the transfer factor of the magnetic field sensor 1 destroy the equality of the transfer factors of both paths so that a small value $\Delta V_h \neq 0$ appears at the output of difference circuit 10.

In this case, correlator circuit 6 correlates the voltage $V_o = V_m + \Delta V_h$ with the voltage $V_G$. If the fields $H_h$ and $H_m$ have no frequency components in common (for example if $H_m$ has a frequency which is an even multiple of the frequency of $H_h$), the output of the correlator 6 is dependent on the correlation between $\Delta V_h$ and $V_G$. This correlation depends upon fluctuations introduced into $\Delta V_h$ as a result of fluctuations in the transfer characteristic of magnetic field sensor 1. Illustratively, if $\Delta V_h$ is zero, the output $V_K$ of the correlator 6 is zero. On the other hand, if $\Delta V_h$ is nonzero, the regulating voltage $V_S$ produced by regulator 7b, in turn, adjusts the value of the transfer coefficient of magnetic field sensor 1 in such a way that the voltage $\Delta V_h$, again, becomes equal to zero and, thereby, the effects of temperature and aging in the transfer factor of magnetic field sensor 1 are compensated.

The attenuator 11 may, for example, comprise one voltage divider comprising two resistances. The circuit according to FIG. 2 thus has the advantage that its output voltage no longer comprises the voltage $V_h$ originated by the auxiliary magnetic field $H_h$ but only difference voltage $\Delta V_h$ that, for practical purposes, is negligible. There thus exists no auxiliary voltage $V_h$ at the output of the circuit represented in FIG. 2 that could disturb further processing of the desired output signal $V_m$ which is proportional to $H_m$, the magnetic field to be measured. In addition, the transfer factor of correlator 6 need no longer be very stable since it only detects the regulating difference. Also the output voltage $V_G$ of the voltage generator 3 need not be very stable.

The circuits represented in FIGS. 1 and 2 put great demands on correlator 6 because of the relatively high voltage $V_m$ at the first input 8 of correlator 6. In order to reduce these requirements, it is of advantage to use one of the circuits represented in FIG. 3 and FIG. 4.

Figure 3:
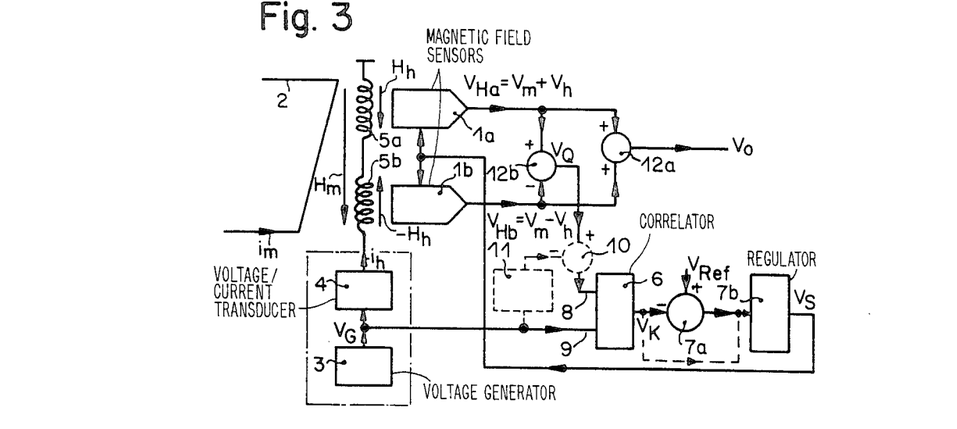
FIG. 3 shows a block diagram of a third variant of such a circuit in accordance with an illustrative embodiment of the invention.

In the arrangement represented in FIG. 3, the coil 5 comprises two approximately equal partial coils 5a and 5b. An approximately identical magnetic field sensor 1a or 1b has been attributed to each of the partial coils 5a, 5b respectively. The output of each of the magnetic field sensors 1a, 1b is connected to an input of adder circuit 12a. The two partial coils 5a and 5b which are, for example, electrically connected in series, are fed by the voltage/currrent generator 3;4 with the same current $i_h$, to produce the auxiliary magnetic fields $H_h$ and $-H_h$, respectively, which both have the same absolute value but opposite directions. The outputs of both magnetic field sensors 1a and 1b are, in a first variation, connected to the input of a difference circuit 12b, whose output $V_Q$ becomes the input 8 to the corrrelator circuit 6. Correlator 6 is used to produce an output voltage $V_K$ dependent on the correlation between $V_Q=2V_h$ and $V_G$.

The control inputs of the magnetic field sensors 1a, 1b are connected to each other and to the output of regulator 7b. The output of correlator 6, in this first variant, is connected to the minus input of the first difference circuit 7a whose other input is a reference voltage $V_{Ref}$. The voltage $V_{Ref}$ illustratively equals the voltage $V_K$ when there are no fluctuations in the transfer characteristic of the magnetic field sensor to disturb the correlation between $V_Q$ and $V_G$. When there are such fluctuations $V_K$ and $V_{Ref}$ are not equal and the output of the difference circuit 7a is fed to the regulator circuit 7b.

In a second variant, that has been represented in FIG. 3 as a dotted line, the difference circuit 7a is not utilized. Instead, the second difference circuit 10 and the attenuator 11 are provided. The output of the third difference circuit 12b is connected to the plus input of the second difference circuit 10 and the output of the attenuator 11 is connected with the minus input of the second difference circuit 10, whose output, in turn, is connected with the first input 8 of correlator 6. The input of attenuator 11 is connected to the voltage output $V_G$ of voltage/current generator 3;4.

Assuming that the transfer factors of the partial coils 5a and 5b, on the one hand, and those of the magnetic field sensors 1a and 1b, on the other hand, are equally large, the following equations will prevail for the switching arrangement represented in FIG. 3:

$$V_{Ha}=V_m+V_h,$$

$$V_{Hb}=V_m-V_h,$$

$$V_o=V_{Ha}+V_{Hb}=(V_m+V_h)+(V_m-V_h)=2V_m \text{ and}$$

$$V_Q=V_{Ha}-V_{Hb}=(V_m+V_h)-(V_m-V_h)=2V_h,$$

wherein $V_{Ha}$ and $V_{Hb}$ are the output voltages for the magnetic field sensors 1a and 1b, $V_m$ is the voltage corresponding magnetic field $H_m$ to be measured and $V_h$, $-V_h$ are the voltages corresponding to the auxiliary magnetic fields $H_h$ or $-H_h$ at the outputs of the magnetic sensors 1a or 1b respectively. $V_Q$ represents the output voltage of the third difference circuit 12b. In the above case of an equally large transfer characteristic of the magnetic field sensors 1a and 1b, the output voltage $V_o$ of the circuit represented in FIG. 3 does not contain the voltages $V_h$ or $-V_h$ originated by the auxiliary magnetic $H_h$ or $-H_h$. In addition, the voltages at the inputs of the correlator 6 in both circuit variants of FIG. 3 does not contain the voltage $V_m$ so that high demands are not placed on the dynamics of correlator 6.

Figure 5:
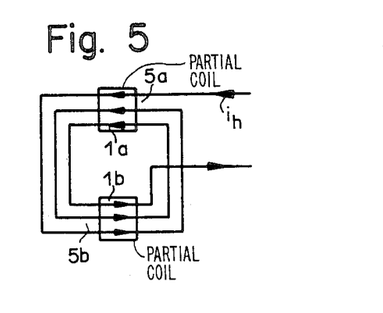
FIG. 5 comprises a sketch of a spatial arrangement of two magnetic field sensors and a flat coil.

The two partial coils 5a and 5b are, for example, each part of a common coil 5. They comprise, for example, as shown in FIG. 5, parallel conductors that are traversed by the auxiliary current $i_h$, furnished by the voltage/current generator 3;4, wherein the direction of flow of the current in the two partial coils 5a and 5b is parallel and oppositely directly. In the representation of FIG. 5, the direction of current flow in the partial coil 5a is from right to left and in the partial coil 5b from left to right.

The coil 5 or the partial coils 5a and 5b of the arrangements represented in FIGS. 1 to 4 may, for example, be a flat coil which is arranged on the surface of a semiconductor body in which the magnetic field sensor 1 or 1a/1b are formed. The flat coil may, for example, have a spiral form and have approximately rectangular windings. Such a flat coil traversed by the auxiliary current $i_h$ has been represented in FIG. 5. If the flat coil represented in FIG. 5 is used in combination with the switching circuit illustrated in FIG. 3, then the two parts of the flat coil that lie diametrically opposite each other each represent a partial coil 5a or 5b, to which there is attributed a corresponding magnetic field sensor 1a or 1b. As can be easily seen in FIG. 5, the conductors of each of the partial coils 5a and 5b are parallel, and they are traversed inside by the same auxiliary currenty $i_h$. Here, the auxiliary current $i_h$ has a value smaller than or equal to about 1 mA.

Figure 4:
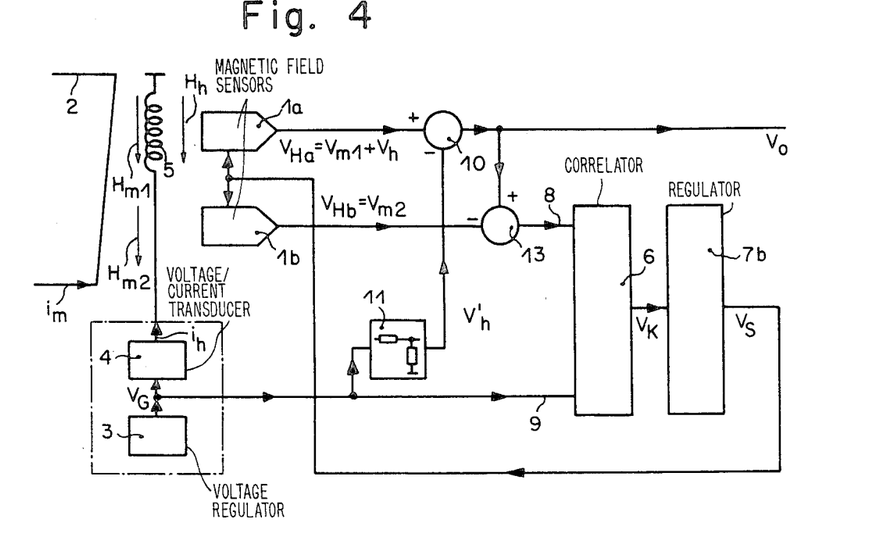
FIG. 4 shows a block diagram of a fourth variant of such a circuit in accordance with an illustrative embodiment of the invention.

The circuit illustrated in FIG. 4 is similar to the circuit illustrated in FIG. 2, with the exception that the output of the second difference circuit 10 (which is the output $V_o$ of the arrangement) is not directly connected to the first input 8 of correlator 6 but instead is connected to the plus input of a fourth difference circuit 13. In addition to the first magnetic field sensor 1a, to which coil 5 is attributed, there is arranged yet a second magnetic field sensor 1b, which detects only the magnetic field $H_m$ to be measured, and to which no coil has been attributed. The output of the second magnetic field sensor 1b is connected to the minus input of the difference circuit 13 whose output is in turn connected to the input 8 of the correlator circuit 6. The voltage output $V_G$ of voltage/current generator 3;4 is connected by way of attenuator 11 to the minus input of the second difference circuit 10, whose output is in turn connected to the plus input of difference circuit 13. The voltage $V_G$ is also connected to the input 9 of the correlator circuit 6.

The following equations apply for the switching-circuit illustrated in FIG. 4:

$$V_{Ha}=V_{m1}+V_h,$$

$$V_{Hb}=V_{m2},$$

$$V_o=V_{Ha}-V'_h=V_{m1}+(V_h-V'_h)$$

$$V_8=V_{Ha}-V'_h-V_{Hb}=V_{m1}+V_h-V'_h-V_{m2}=(V_{m1}-V_{m2})+(V_h-V'_h)$$

wherein $V_{m1}$ is the voltage produced by sensor 1a as a result of the local value $H_{m1}$ of the magnetic field to be measured. $V_{m2}$ is the voltage produced by sensor 1b as a result of the local value $H_{m2}$ of the magnetic field to be measured. $V_h$ is the voltage produced by the sensor 1a as a result of the auxiliary magnetic field $H_h$ and $V'_h$ is the voltage at the output of attenuator 11 (see FIG. 4). $V_8$ represents the voltage at the first input 8 of correlator 6.

The correlator 6 and regulator 7b act in a manner to maintain the difference voltage:

$$\Delta V_h = V_h - V'_h = 0$$

and thereby $$V_o = V_{m1} \text{ and}$$

$$V_8 = V_{m1} - V_{m2}$$

These equations show that, in contrast to FIG. 3, even with an asymmetry in the magnetic field sensors 1a, 1b, i.e. with any difference in the $V_{m1}$ and $V_{m2}$ voltages, the output voltage $V_o$ will not contain any disturbing auxiliary voltage $\Delta V_h$. However, improved performance may result, including improved performance of the correlator circuit 6 when the magnetic field sensors 1a, 1b are identical.

Figure 6:
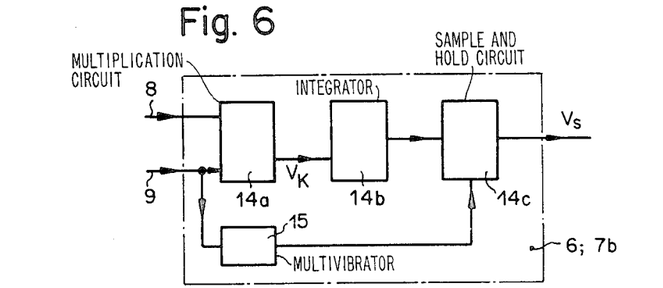
FIG. 6 shows a block diagram of a first variant of a correlator/regulator circuit in accordance with an illustrative embodiment of the invention.
Figure 7:
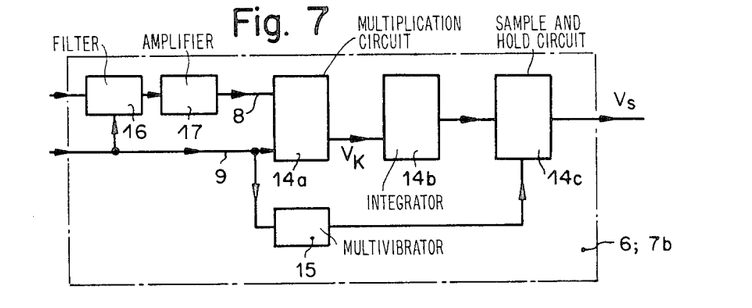
FIG. 7 shows a block diagram of a second variant of a correlator/regulator circuit in accordance with an illustrative embodiment of the invention.

The signals issuing from output voltage $V_G$ of voltage/current generator 3;4 may have any desired form. With a rectangular output voltage $V_G$, correlator 6 may be especially simple to realize. The directly connected circuits 6;7b of FIG. 2 and FIG. 4, and the second variant of FIG. 3 may be implemented using the correlator/regulator circuits represented in FIGS. 6 and 7. FIGS. 6 and 7 show a multiplication circuit 14a with an integrator 14b connected to the output of the multiplication circuit. The output of integrator 14b is connected by way of a "sample and hold circuit" 14c to the control input of the magnetic field sensors 1 or 1a and 1b.

The second input 9 of the correlator/regulator circuit of FIGS. 6, 7 is connected by way of a monostable multivibrator 15 to the control input of the sample/hold circuit 14c. The multiplication circuit 14a may, for example, comprise a simple polarity reversal switch. The input signal at the first input 8 of the correlator/regulator circuit 6;7b has its polarity reversed synchronously with the regulator output voltage $V_G$ of the voltage/current generator 3;4 and is thereby multiplied by the output voltage $V_G$. The sample and hold circuit 14c samples the output voltage of integrator 14b once per period of output voltage $V_G$. In effect the integrator 14b serves to take the average of the products of the multiplication once each period of the voltage signal $V_G$. Only certain frequency components will survive the integration and contribute to the average. Other frequency components such as those which are synchronous with or equal to even integral multiples of the frequency of $V_G$ are suppressed. If the frequency of $V_G$ is properly chosen, as discussed below, the non-suppressed components result from non-linearities and/or other fluctuations in the transfer characteristic of the magnetic field sensor. In order to ensure a good suppression, the rise time of the circuit 14c, i.e. the impulse times of the monostable multivibrator 15 should be short. The monostable multivibrator 15 is, for instance, triggered by the positive-running flanks of voltage $V_G$.

Integrator 14b has a triple function: on the one hand, it serves to from the average of the output of its associated multiplication member 14a; then it compares this average value with a reference voltage and finally it functions as an integrating regulator. The setting of the value of the transfer coefficient of the magnetic field sensor 1 or of the magnetic field sensors 1a and 1b has to be effected with the aid of an integrating regulator, in order that the static error of the regulator will acqurie a value of zero.

The dynamics of the circuit illustrated in FIG. 6 can be improved by the circuit illustrated in FIG. 7, which is set up in a way similar to that represented in FIG. 6, with the exception that here there is a filter 16 and a subsequent amplifier 17 which are connected to the first input 8 of the correlator/regulator circuit 6;7b. The filter 16 may, for example, in the case of a rectangular output voltage $V_G$ be a synchronous two-path filter which is controlled by the output voltage $V_G$ of the voltage generator 3;4. Filter 16 suppresses the voltage $V_m$ that is produced by the magnetic field $H_m$ to be measured, if the voltage $V_m$ is present at the input 8 of the correlator/regulator. However, it is undesirable for the filter 16 to dampen the voltages $V_h$ or voltages $V_h$ and $-V_h$. Since the total amplitude of these voltages may be smaller after the filter 16, they have to be amplified by the amplifier 17. This additional amplification enables a gain in the dynamics of the correlator.

Figure 8:
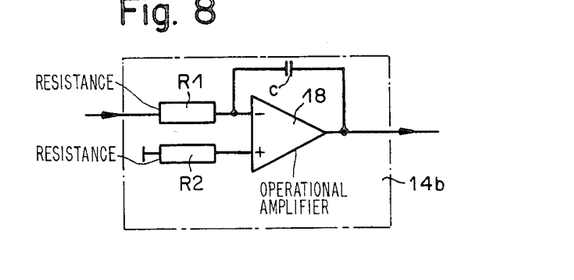
FIG. 8 is a printed circuit diagram for an integrator circuit.

Integrator 14b represented in FIG. 8 comprises a known operational amplifier 18. The output of operational amplifier 18 is fed back by way of a capacitor C to its inverting input. The inverting input is connected by way of a resistance R1 to a first input of the integrator. The non-inverting input of operational amplifier 18 is connected by way of an equally large resistance R2 to ground.

Preferably, two conditions should be fulfilled for the form of signal for the output voltage $V_G$ of voltage generator 3;4 and for the form of signal for the auxiliary magnetic fields $H_h$ and $-H_h$:

The signals $V_G$, $H_h$, $-H_h$ should not have any frequency component in common with the magnetic field $H_m$ to be measured and The signals $V_G$, $H_h$, $-H_h$ should have a frequency band which resembles that of the magnetic field $H_m$ to be measured to an extent such that the transer characteristic of the magnetic field sensors 1, 1a and 1b for the magnetic fields $H_m$, $H_h$ and $-H_h$ are equally large.

The simplest form for the signals $i_h$ and $V_G$ delivered by voltage generator 3;4 is a rectangular signal limited to an appropriate frequency band. In this case, the correlator 6 can be realized in an especially simple manner as described above. Frequency overlap between the signals $i_m$, $H_m$, $V_m$, and the signals $V_G$, $i_h$, $H_h$, $-H_h$ can be simply prevented as follows. The signals $i_h$ and $V_G$ should be rectangular in form and have a frequency such that the frequency of the current $i_m$ or of the magnetic field $H_m$ to be measured equals an even numbered multiple of the frequency of the rectangular signals $i_h$ or $V_G$. In an electricity meter, for example, the voltage $V_G$ may be generated by determining the base wave of the system voltage using a comparator of a Schmitt-Trigger and thereafter dividing the frequency of the thus obtained rectangular voltage by an even number.

If one of the described switching arrangements is used in an electronic electricity meter, then, with an intent to defraud, attempts could be made to falsify the measurement result of the electricity meter by causing, through control of the system load, the even-numbered harmonic waves of the system frequency to be amplified. This could result in portions of the current $i_m$ which have the same or a similar form of signal as the voltage $V_G$. This can be prevented by one of the following counter-measures:

To use as output signals $V_G$ and $i_h$ of the voltage/current generator 3;4 a pseudo-random sequence of impulses that is synchronous of asynchronous with the system voltage.

The output signal $V_G$ and $i_h$ of voltage generator 3;4 are, sporadically or periodically, switched off during certain periods, wherein before each switching-off the last prevailing value of the output voltage $V_S$ of regulator 7b is stored with the aid of another sample-and-hold circuit. The portion of the output signal $V_o$ corresponding to the signal $i_h$ or $V_G$ of the output voltage $V_o$ of the switching circuit can be determined during the turn-off time, as by comparing the voltage $V_o$ before and after turn-off. This voltage level may now either be controlled or, when a certain predetermined, acceptable limit is exceeded, release an alarm signal, or be automatically taken into consideration as an offsetting voltage during regulation, i.e. be subtracted.

Finally, the above described embodiments of the invention are intended to be illustrative only. Numerous alternative embodiments may be devised by those skilled in the art without departing from the spirit and scope of the following claims.

We claim:

1. A circuit for compensating for fluctuations in the transfer characteristics of a magnetic field sensing means, said circuit comprising:
   coil means for generating an auxiliary magnetic field superimposed on a magnetic field to be measured by said magnetic field sensing means ; said coil means comprising two approximately equal partial coils;
   said magnetic field sensing means comprising two approximately identical magnetic field sensors associated with the respective partial coils;
   an additional circuit connected to the outputs of said magnetic field sensors for adding the output signals of said magnetic field sensors;
   a voltage generator and voltage to current transducer for supplying current to said partial coils, said partial coils producing two auxiliary magnetic fields virtually the same value but in opposite directions;
   a difference circuit connected to the outputs of said magnetic field sensors for taking the difference of the two output signals of said magnetic field sensors;
   correlator means for correlating a voltage resulting at least in part from the detection of the auxiliary magnetic field by the magnetic field sensing means and an output voltage of said voltage generator; one input of said correlator means being coupled to said difference circuit;
   means for connecting said correlator means to said voltage generator
   regulator means capable of producing a control signal in response to said correlator means;
   means for connecting said regulator means to said magnetic field sensing means; and
   said correlator means being connected to a control input of said magnetic field sensing means, thereby to control the transfer characteristics of said magnetic field sensing means.

2. A arrangement according to claim 1, wherein the two partial coils each are part of a common coil and wherein each of the partial coils comprises parallel conductors that are traversed in opposite directions by a current produced by said voltage to current transducer.

3. A circuit according to claim 1, characterized in that the regulator means is an integrating regulator.

4. A circuit according to claim 1, wherein said correlator and said regulator together comprise a multiplication circuit which is connected to an integrator, said integrator being connected with the control input of the magnetic field sensing means by way of a sample and hole circuit, a control input of the sample and hold circuit being activated by a monostable multivibrator that is directly connected to said output of the voltage generator.

5. A circuit according to claim 4, wherein the multiplication circuit is a polarity reversing switch.

6. A circuit according to claim 5 wherein said correlator and regulator further comprise a filter and an amplifier connected to said filter, said amplifier also being connected to an input of said correlator means.

7. A circuit according to claim 1 characterized in that the output signal of the voltage generator is rectangular.

8. A circuit according to claim 7, wherein the frequency of the base wave of said magnetic field to be measured is an even-numbered multiple of the frequency of said rectangular signal.

9. A circuit according to claim 7, wherein the output signal of the voltage generator is a pseudo-random sequence of impulses.

10. A circuit for compensating for fluctuations in the transfer characteristics of a magnetic field sensing means, said circuit comprising:
    coil means for generating an auxiliary magnetic field superimposed on a magnetic field to be measured by said magnetic field sensing means;
    said magnetic field sensing means comprising two approximately identical magnetic field sensors;
    a voltage generator and voltage to current transducer for supplying current to said coil means;
    a first difference circuit connected to the outputs of said magnetic field sensors for taking the difference of the two output signals of said magnetic field sensors;
    correlator means for correlating a voltage resulting at least in part from the detection of the auxiliary magnetic field by the magnetic field sensing means and an output voltage of said voltage generator; one input of said correlator means being coupled to said difference circuit;
    means for connecting said correlator means to said voltage generator;
    regulator means capable of producing a control signal in response to said correlator means;
    means for connecting said regulator means to said magnetic field sensing means;
    said correlator means being connected to a control input of said magnetic field sensing means, thereby to control the transfer characteristics of said magnetic field sensing means;
    one magnetic field sensor detecting both the auxiliary magnetic field and the magnetic field to be measured and the other magnetic field sensor detecting only the magnetic field to be measured; the output of the one magnetic field sensor being connected to the plus input of a difference circuit while the other input of said second difference circuit being connected through an attenuator to said voltage generator;
    the output of said second difference circuit being connected to an input of said first difference circuit which has its other input connected to the output of said other magnetic field sensor and the output of said other magnetic field sensor being connected to the input of said correlator means.

11. A method for compensating for fluctuations in the transfer characteristic of a magnetic field sensing means comprising the steps of
(a) generating a voltage by means of a voltage generator and converting said voltage to a current,
(b) utilizing said current to generate an auxiliary magnetic field, which is superimposed on a magnetic field to be measured by said sensing means,
(c) correlating a signal resulting at least in part from the detection of said auxiliary magnetic field by said sensing means with said voltage of said voltage generator,
(d) producing a regulating voltage in response to said correlating step for controlling the transfer characteristic of said sensing means,
(e) switching said voltage generator off, temporarily,
(f) storing the last value of said regulating voltage in a sample and hold circuit before switching said voltage generator,
(g) using the output signal from said magnetic field sensing means to determine an offset voltage corresponding to the voltage or current associated with said voltage generator, and
(h) coupling the offset voltage to said sensing means.

* * * * *

UNITED STATES PATENT AND TRADEMARK OFFICE
CERTIFICATE OF CORRECTION

PATENT NO. : 4,752,733

DATED : June 21, 1988

INVENTOR(S) : Jan Petr and Heinz Lienhard

It is certified that error appears in the above-identified patent and that said Letters Patent is hereby corrected as shown below:

ON THE TITLE PAGE INSERT:

-- [73]     Assignee :   LGZ Landis & Gyr Zug AG of Zug, Switzerland --.

Item [30] should read

-- [30]    Aug. 16, 1984 [CH] Switzerland ---- 03 935/84 --.

Signed and Sealed this

Seventeenth Day of January, 1989

Attest:

DONALD J. QUIGG

*Attesting Officer*      *Commissioner of Patents and Trademarks*